United States Patent [19]

Frazer

[11] 4,176,662

[45] Dec. 4, 1979

[54] APPARATUS FOR ENDOSCOPIC EXAMINATION

[75] Inventor: Robert E. Frazer, La Canada, Calif.

[73] Assignee: The United States of America as represented by the Administrator of the National Aeronautics and Space Administration, Washington, D.C.

[21] Appl. No.: 807,597

[22] Filed: Jun. 17, 1977

[51] Int. Cl.² .................. A61B 1/06; A61M 25/00
[52] U.S. Cl. ............................. 128/6; 128/348;
128/DIG 9; 138/33; 138/103; 138/133; 219/201; 219/522
[58] Field of Search ............... 128/4, 5, 6, 7, 8, 348,
128/349 R, 2 M, DIG. 9, 2 V, 2 P, 2.1 A, 349 BV, 350 R, 351, 401, 214 A, 343; 138/33; 219/522

[56] References Cited

U.S. PATENT DOCUMENTS

| | | | |
|---|---|---|---|
| 2,243,992 | 6/1941 | Wappler | 128/8 |
| 2,758,194 | 8/1956 | Heron | 219/522 |
| 2,793,280 | 5/1957 | Harvey | 219/301 |
| 2,855,934 | 10/1958 | Paughaday Jr. | 128/349 R |
| 3,378,673 | 4/1968 | Hopper | 138/33 |
| 3,665,928 | 5/1972 | Del Guercio | 128/350 R |
| 3,828,112 | 8/1974 | Johansen et al. | 138/127 |
| 3,847,157 | 11/1974 | Caillovette et al. | 128/2 M |
| 3,895,637 | 7/1975 | Choy | 128/348 |
| 3,896,793 | 7/1975 | Mitsui et al. | 128/6 |
| 3,948,251 | 4/1976 | Hosond | 128/4 |

FOREIGN PATENT DOCUMENTS 2140994  2/1973 Fed. Rep. of Germany .............. 128/6
1278965 11/1961 France .................................. 128/349 R

OTHER PUBLICATIONS

Jacobson, B. Servo Tracks Pills in Human Body, Electronics, Mar. 22, 1963, pp. 58–60.

*Primary Examiner*—Robert W. Michell
*Assistant Examiner*—Arthur S. Rose
*Attorney, Agent, or Firm*—Monte F. Mott; John R. Manning; Wilfred Grifka

[57] ABSTRACT

An endoscope is disclosed having a propulsion mechanism and at least one transmitter at the distal end transmitting bursts of energy waves (radio frequency or ultrasonic) for tracking the position of the distal end through the use of two or more transducers on the anterior or lateral surfaces of a patient. The propulsion mechanism may consist of two radially expandable bladders separated by an axially expandable bellows with only the forward bladder attached to the distal end so that by expanding and contracting them in proper sequence, propulsion of the endoscope is achieved. Alternate mechanisms comprise compliant paddles on the distal end directly on an articulated section, or compliant paddles on a rotatable sleeve on the distal end. The endoscope has a sheath which includes material having a sharp melting point slightly above body temperature so that the sheath may be made flexible at selected sections by applying current to separate heating wires in the sections of the sheath.

2 Claims, 10 Drawing Figures

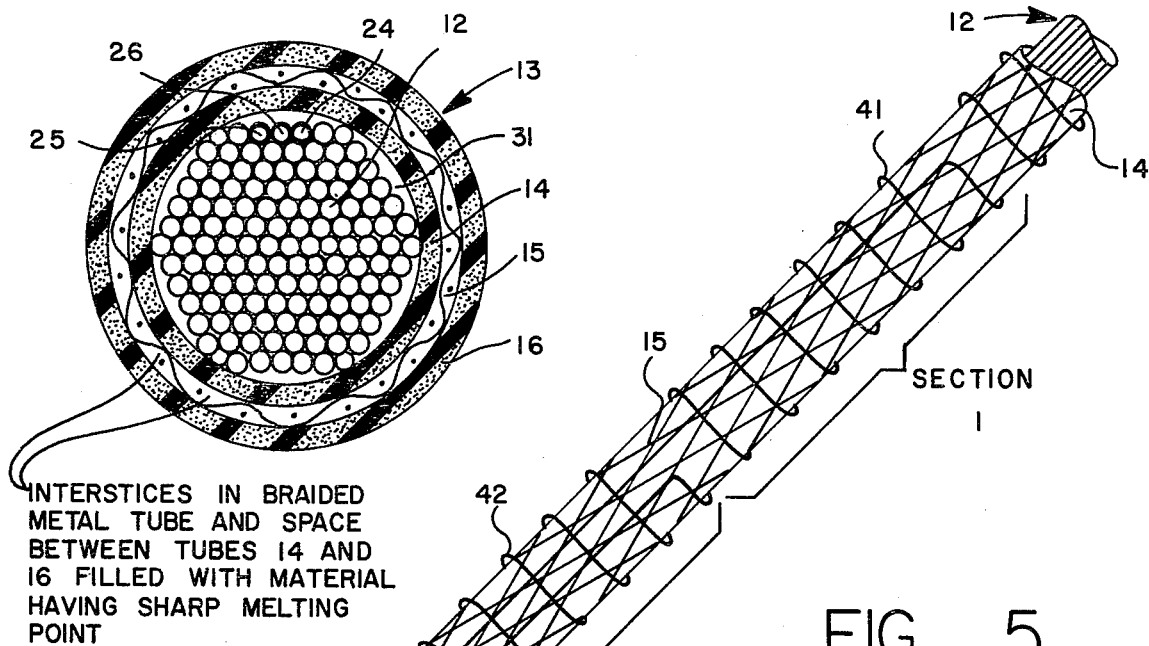
FIG. 2
INTERSTICES IN BRAIDED METAL TUBE AND SPACE BETWEEN TUBES 14 AND 16 FILLED WITH MATERIAL HAVING SHARP MELTING POINT
FIG. 5
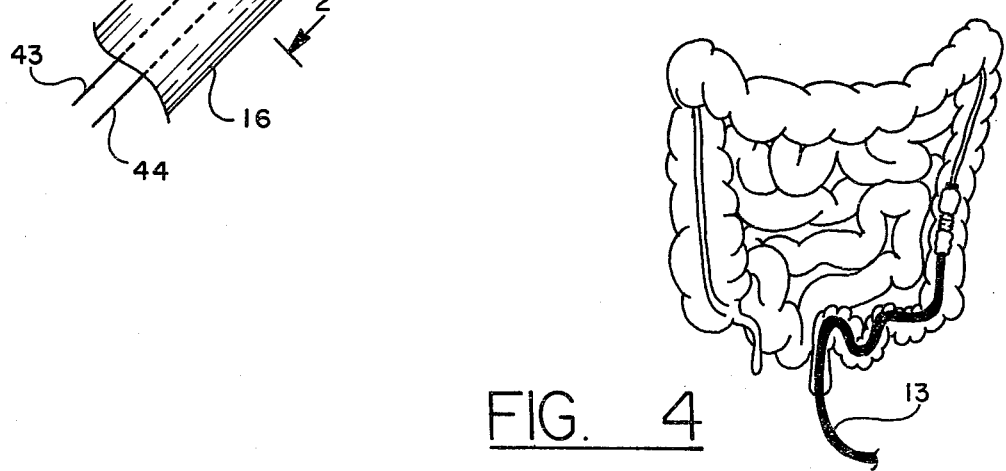
FIG. 4

APPARATUS FOR ENDOSCOPIC EXAMINATION

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

BACKGROUND OF THE INVENTION

This invention relates to an endoscope and more particularly to an endoscope having an articulated section and a propulsion mechanism at the distal end.

There is a growing need for gastrointestinal endoscopes, and particularly for an endoscope with increased flexibility for passage through the sigmoid colon and beyond. In the past, colonoscopes using fiber optics have been comprised of a somewhat rigid conduit for bundles of optical fiber, feed lines for air or fluid and a channel for suction and forceps. One bundle of fibers provide light guides for illumination and another provides a return image guide. The distal end includes an articulated or bending section which permits the distal end to be turned through arcs of from 200° to 300°, up and down and sideways, by remote-controlled operation for observation over more than a hemisphere in front of the endoscope as it is inserted.

Insertion is achieved by manually forcing the somewhat rigid conduit and controlling the arc of the articulated section at the distal end. The result is that the sigmoid colon is stretched and distorted in the process of inserting the endoscope past the first turn. Similar problems occur in esophageal stenosis endoscopy. It would be desirable to provide a more flexible conduit for the endoscope with a propulsion mechanism at the distal end which will pull or drag a flexible conduit, and to further provide a system for tracking the position of the distal end of the endoscope in order that the endoscope traverse the sigmoid and splenic flexures without undue discomfort and risk to the patient while knowing the position of the distal end at all times.

SUMMARY OF THE INVENTION

In accordance with the invention, an endoscope is provided with a propulsion mechanism at the distal end, and with an energy (electromagnetic or ultrasonic) wave transmitter at the tip of the distal end. An array of two or more transducers placed outside of the patient receives the transmitted waves for determination of the position of the endoscope tip in the patient. The propulsion mechanism is comprised of two inflatable, radially expandable, annular bladders separated by an annular, inflatable, axially expandable bellows over the distal end of the endoscope. One bladder is connected to the tip of the endoscope while the bellows and the other bladder are connected in tandem to the one bladder in order to be free to move along the length of the endoscope. By programming the radial expansion and contraction of the bladders and the axial expansion and contraction of the bellows, it is possible to propel the distal end of the endoscope through a body passage of a patient. While one bladder is inflated, the bellows is expanded under air pressure to move the other uninflated bladder to a new position where it is inflated. The one bladder is then deflated, and the bellows is contracted. The process is repeated for propulsion in one direction. For propulsion in the opposite direction, the order of inflating and deflating the bladders is reversed. Tubes for inflating and deflating the bladders under air pressure are included in a sheath which extends from the distal end back to the proximal end of the endoscope. A tube for expanding and contracting the bellows under air pressure is similarly included in the sheath.

An alternate propulsion method employs an array of compliant paddles, either directly on an articulated or bending section of the endoscope at the distal end, or on a rotatable sleeve over the distal end. In either case, the profile of the paddles is a gentle curve from the front to the back, and at a small "pitch" angle to the axis of the endoscope. The sleeve is rotated by a gear at the end of a flexible shaft in the sheath. The shaft gear engages a ring gear at the front end of the paddle sleeve.

Rigidity of the endoscope is controlled in sections in order for it to be compliant enough to pass readily through a tortuous path, yet rigid enough to transmit external movements when that is desired. Rigidity control is achieved by forming the sheath of an inner plastic tube, a braided metal tube over the inner tube, and an outer tube over the braided metal tube with a material which has a very sharp melting point slightly above body temperature, in the interstices of the braided metal tube and the space between the plastic tubes. The different sections of the sheath are provided with sections of insulated heating wires wound around the braided metal tube, and separate insulated wires to the different heating sections for control of current from the proximal end of the endoscope.

The novel features that are considered characteristic of this invention are set forth with particularity in the appended claims. The invention will best be understood from the following description when read in connection with the accompanying drawings.

BRIEF DESCRIPTION OF THE DRAWINGS

FIG. 2 is a cross section of the endoscope sheath.

FIG. 4 is a diagram illustrating the path of an endoscope through the sigmoid colon.

FIG. 5 illustrates a portion of the endoscope of FIG. 1 with an outer plastic tube cut away to expose sectional heating coils.

DESCRIPTION OF PREFERRED EMBODIMENTS

Figure 1:
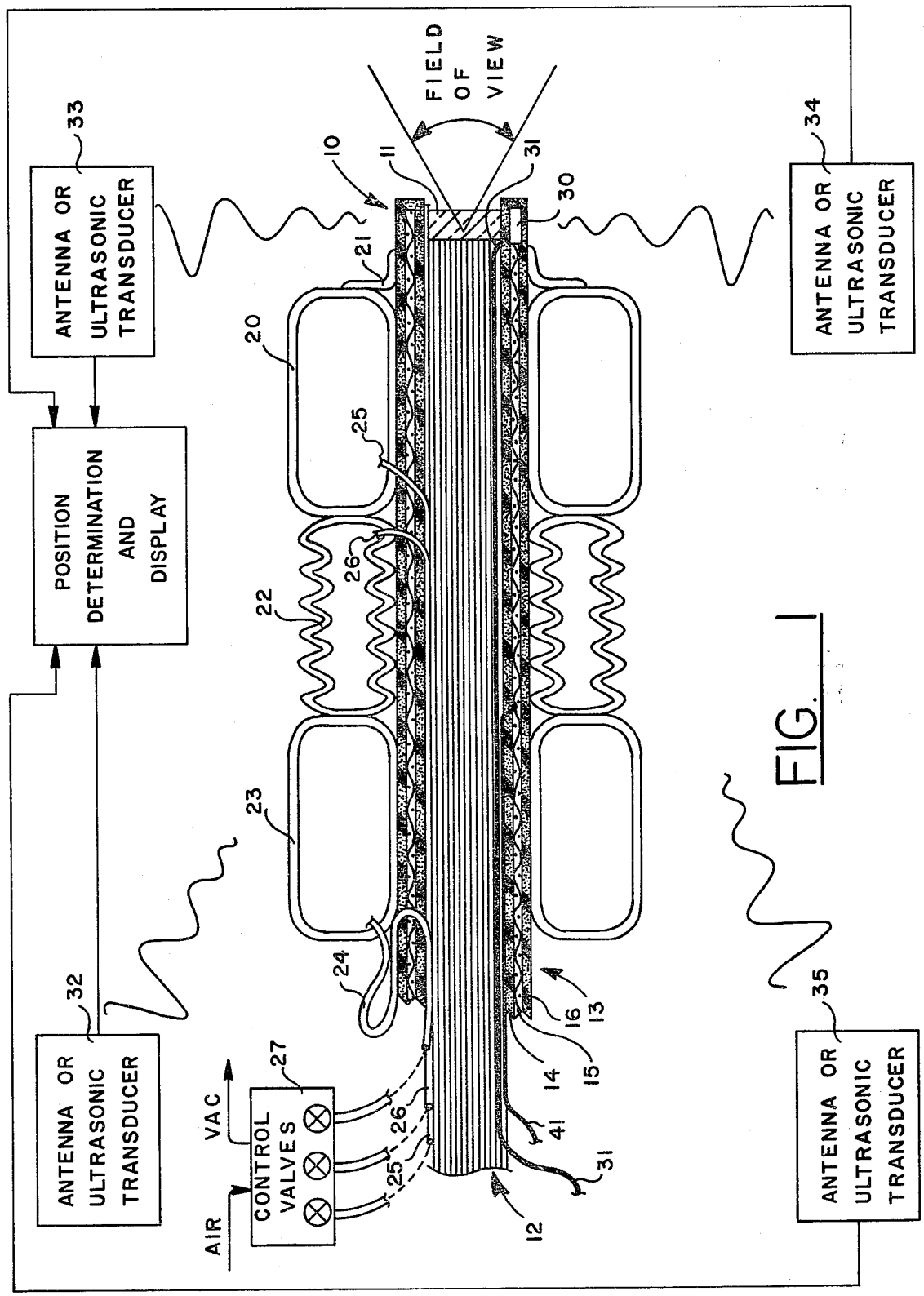
FIG. 1 is a longitudinal sectional view of the distal end of an endoscope equipped with a propulsion mechanism and with a transducer for emitting waves to a tracking system, all according to the present invention.

Referring now to FIG. 1 of the drawings, there is shown the distal end 10 of an endoscope having a window 11 coupled to the proximal end (not shown) by bundles of optical fibers 12, some of which are used to transmit light from an external source through the window, and others which are used to transmit an image back to the proximal end from the field of view of the window. In addition to the bundles of optical fibers, there may be tubes from the proximal end to the distal end and through the window to provide for blowing air or water into the body passage in front of the window and for suction of air and fluid. There may even be a tube for passing forceps into the body passage and for suction of body tissue. All of these tubes, and others to be specifically referred to hereafter, are sufficiently flexible to not degrade the flexibility of a sheath 13 which extends from the distal end 10 to the proximal end (not shown). The sheath is comprised of a plastic inner tube 14, a woven metal tube 15 and an outer plastic tube 16, as may be more clearly seen in FIG. 2.

A first inflatable annular bladder 20 is connected to the distal end of the sheath by a plastic web 21, and, if desired, by compliant adhesive material between the bladder and the sheath. The first bladder is fixed in position on the distal end of the sheath.

Figure 3:
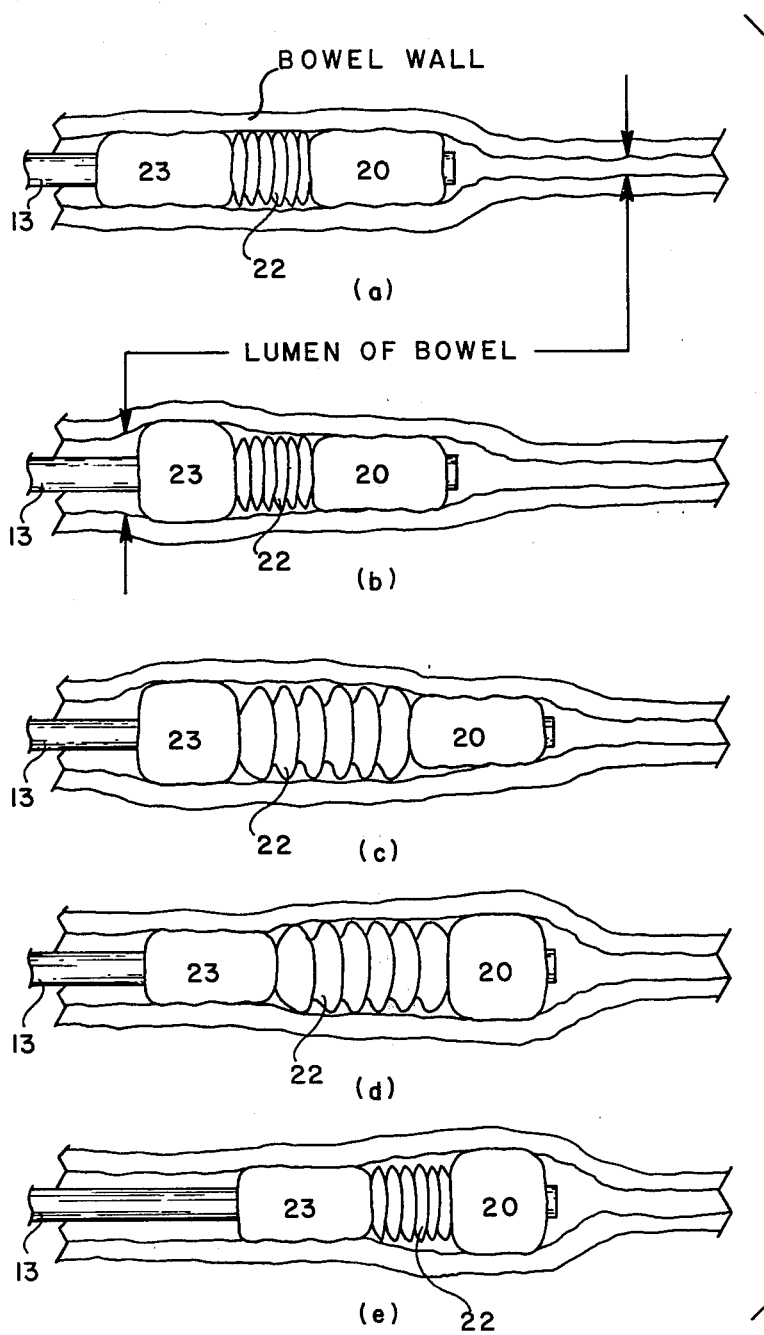
FIG. 3 illustrates the operation of the propulsion mechanism of FIG. 1.

Attached to the rear of the first bladder is a plastic bellows 22 and attached to the rear of the bellows is a second inflatable bladder 23. The bellows and second bladder are not attached to the sheath. Therefore, upon inflating the second bladder while the first bladder is deflated, and then expanding the bellows, the distal end of the endosope is propelled forward as shown in FIGS. 3(a) to 3(c). The first bladder is then inflated to anchor the distal end at a new position while the second bladder is deflated as shown in FIGS. 3(d) and 3(e), and the bellows contracted as shown in FIG. 3(e). The process is repeated to continue to propel the distal end of the endoscope forward. To propel the distal end in the opposite direction, the process is reversed.

The first bladder is inflated and deflated through a tube 24 while the second bladder is inflated and deflated through a separate tube 25. The bellows is expanded and contracted by air pressure through a tube 26. All of these propulsion control tubes are contained in the sheath 13 and are connected at the proximal end to control valves 27 which selectively connect the tubes to air pressure (AIR) or a vacuum (VAC).

A single transducer 30 (FIG. 1) at the distal end periodically transmits a burst of waves, which may be electromagnetic (radio frequency) or acoustic (ultrasonic), under control of a signal conducted over an insulated wire 31. The woven metal tube connected to the transducer functions as a signal return (circuit ground). These waves are detected at a plurality of spaced receivers 32 to 35 comprising an antenna for radio frequency waves or an ultrasonic transducer. The time each burst is received by a receiver relative to other receivers in an indication of its relative distance, thus yielding position data from which the distal end of the endoscope may be continually determined and plotted by means having a cathode ray tube or graph display 36.

FIG. 4 illustrates the tortuous path through which the endoscope must travel when used as a colonoscope. Using this propulsion mechanism at the distal end of the endoscope to pull the flexible sheath through the sigmoid colon is more satisfactory than pushing it through from the proximal end as has been the practice.

In order for the endoscope to follow the tortuous path, the sheath must be flexible, as noted hereinbefore, but when it is necessary for the endoscope to transmit external movements to the distal end, such as for making minor adjustments to the position of the distal end, the sheath must be rigid. These requirements are not compatible, but are made compatible by filling the interstices in the braided metal tube 15, and the space between the inner and outer plastic tubes 14 and 16 of the sheath, with a material having a sharp melting point near body temperature (37° C.). Different sections of the braided metal tube are then wound with separate insulated heating wires, such as wires 41 and 42 wound over short sections 1 and 2 as shown in FIG. 5. The end of each section winding is connected to the woven metal tube which functions as a ground return; and the control wires for each section, such as wires 43 and 44 for section wires 41 and 42, are designed for lower resistance per unit length in order that the controlled current produce a minimum of heat in the control wires.

Warming a selected section a few degrees above body temperature will convert the solid material in that section to a liquid material thus converting it from a stiffening material to a compliant material. Several families of pure polymers, such as polyethyleneglycol, are available in various molecular-weight formulations for different melting points. It is thus a simple matter to select the formulation which yields a melting point of about 38° C. to 39° C. The decision as to which sections should be controlled to be rigid and which should be controlled to be compliant can be guided by the plot made of the position of the distal end.

Figure 6A:
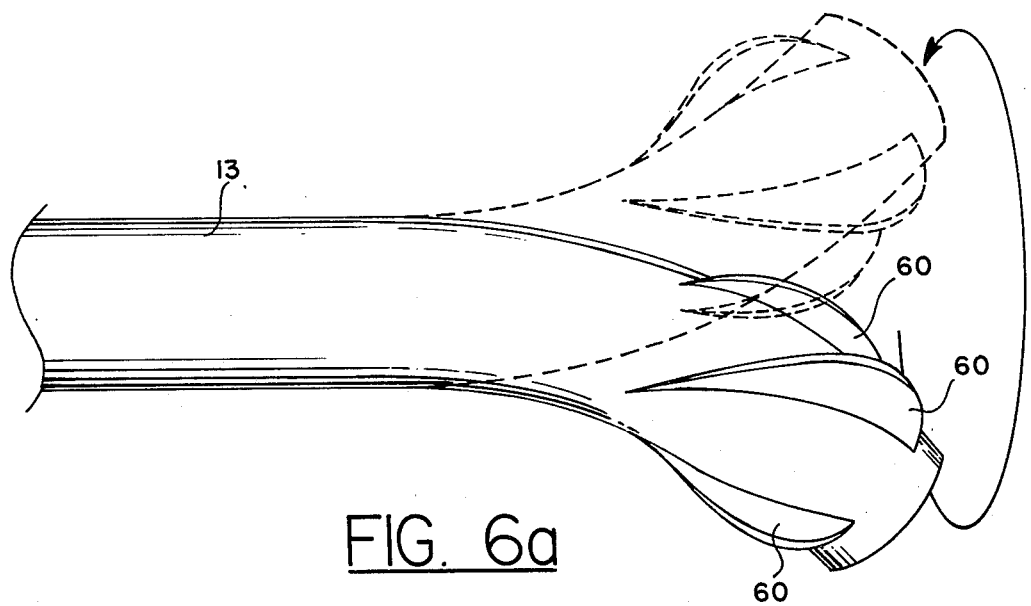
FIG. 6 illustrates an alternate propulsion system.
Figure 6B:
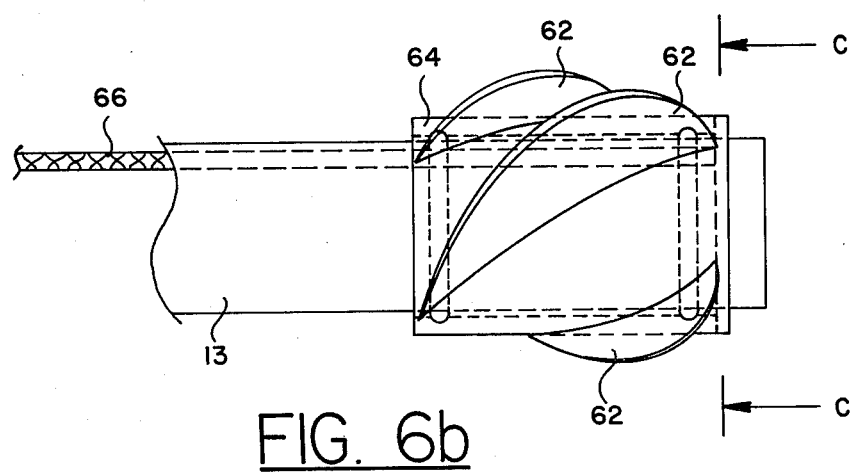

Referring now to FIG. 6a, an alternative propulsion method would use an array of compliant paddles 60 at the distal end of the endoscope along the length of the articulated section. As the articulated section is bent in a conventional manner, as in the Olympus Gastrointestinal Fiberscope Model GIF, type P, manufactured by Olympus Corporation of America, the paddles function like tail fins of a fish in propelling the distal end forward. Still another propulsion mechanism shown in FIG. 6b through 6e is comprised of compliant paddles 62 at the distal end of the endoscope. The paddles would be mounted on a sleeve 64 (FIG. 6e) rotatable about the axis of the instrument. The profile of the paddles would be gently curved front to back and at a small "pitch" angle to the axis.

Figure 6C:
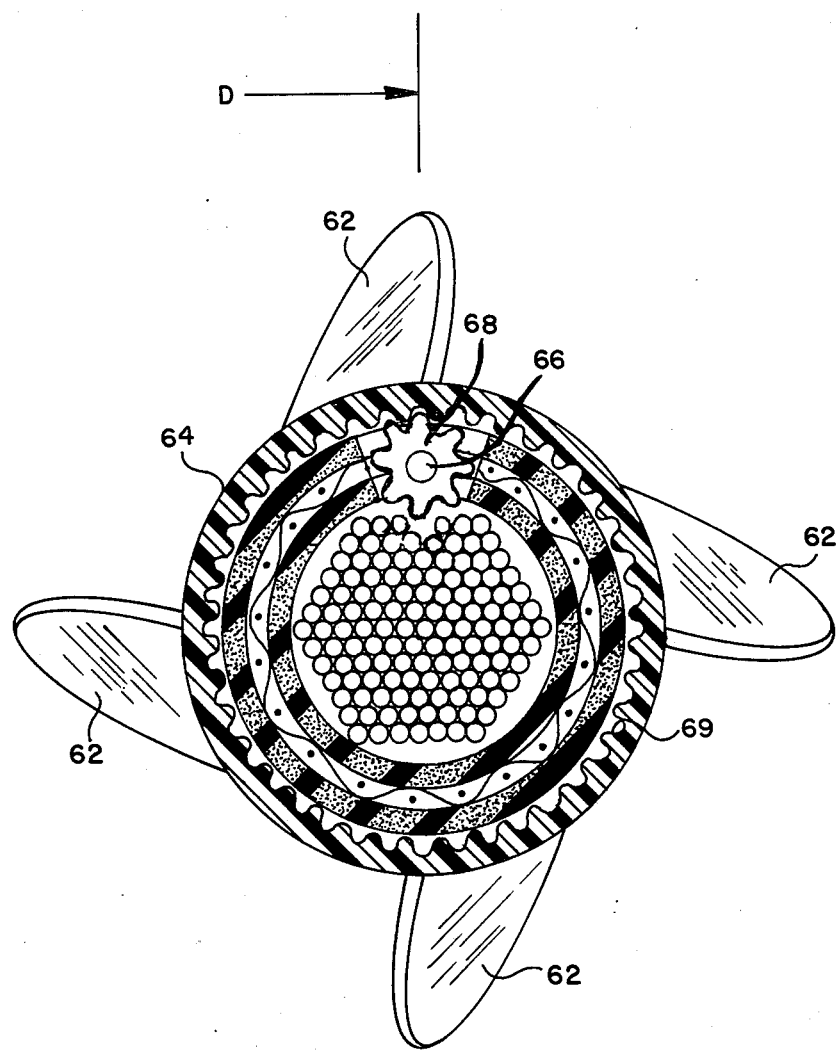
Figure 6D:
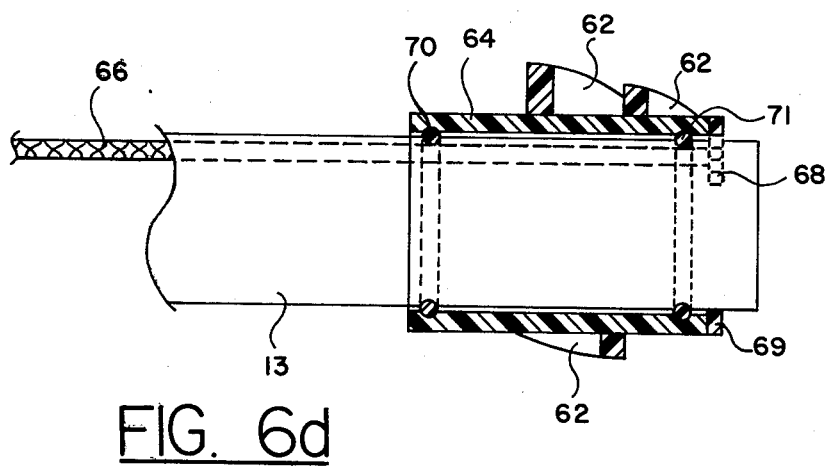
Figure 6E:
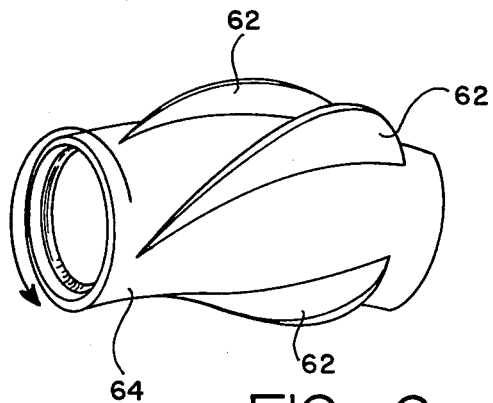

This assembly could be driven in rotation by one of several means. A flexible cable 66 used as a drive shaft is driven externally at its proximal end. At the distal end, the cable 66 is provided with a gear 68 (FIG. 6c) to engage a ring gear 69 as shown in FIG. 6c, a sectional view taken on a line c—c in FIG. 6b. The sleeve 64 itself is compliant so that it may bend with the sheath 13 when necessary, as shown in FIG. 6e. To minimize friction as the sleeve 64 is turned, albeit slowly, O-rings 70 and 71 (FIG. 6d) are fitted between the sheath and the sleeve. The O-ring 70 fits tightly in a groove in the sheath so that it stays in place while the sleeve turns and, as the sheath is bent, moves over the O-ring. The O-ring 71 is slightly larger in cross section and fits tightly in a groove in the sheath and also fits in a groove in the sleeve so that the sleeve may turn on the sheath but not move forward or backward on the sheath. These O-rings and the sleeve 64 may be made of teflon to further reduce friction as the sleeve is rotated.

In summary there has been disclosed a single transmitter on the tip of the endoscope the waves from which can be sensed by an array of two or more receivers on the anterior or lateral surfaces of a patient. The arrival times of a pulse signal from the transmitter at the receivers could be used to generate X and Y coordinates for display. The transmitter position must lie at the intersection of two circles whose centers lie on the receivers and whose radius is proportioned to the elapsed time between the transmitted and received pulse. The proper placement of at least two receivers laterally either low or high on the abdomen would eliminate ambiguity of the indication. For each wave burst transmitted, a point will be defined and displayed for the position of the colonoscope tip. The position of the moving tip can thus be displayed as a series of points or a track on an overlay.

A more accurate indication of the real position of the endoscope can be had by using multiple transmitters along the length of the instrument. Each time a transmitter is excited, its coordinates will be displayed on the CRT. In that case, it is obvious that the transmitters must be driven sequentially because simultaneous excitation would cause interfering arrival times at the receivers. The simplest concept would be to have a separate wire leading from each transmitter in the endoscope to an external sequencing circuit which would energize one wire and its connected transmitter, and then switch to the next transmitter, etc. This system would require a wire for each transmitter, but would be ideal for a few transmitters.

If better position information is required, more transmitters will be needed, and another method for sequentially exciting them may be appropriate to avoid large numbers of wires in an already crowded colonoscope sheath. One option for sequentially pulsing the series of transmitters from a single line involves the use of pulse delaying networks. A pulse "launched" into such a system would activate the first transmitter to emit a wave burst. After a short time the original electrical pulse will propagate through the delay network and activate the second transmitter. This process would continue through the series of transmitters generating a wave burst at each transmitter. The coordinates of each pulsed transmitter will be displayed as before on the CRT. The resulting display will depict the real time position of the endoscope during every pulse sequence. The detail in this display will be a function of the number of transmitters which can be incorporated in the endoscope and successfully driven.

Alternate implementations which are feasible include the use of ultrasonic crystals as transmitters with separate and narrow resonances which would permit sequential excitation from a single line driven with trains of signals at the resonant frequencies of the crystals. All systems based on ultrasound must operate within certain constraints which appear to be compatible with the endoscope disclosed. The spatial resolution of the system improves with increased frequency of the transmitting crystal. A resolution of approximately one millimeter is typical for a 10 megahertz ($10^6$) frequency. This resolution is more than adequate for this application. Crystal size is smaller for higher frequencies—about 6–7 millimeters diameter is typical for a 10 megahertz oscillator. This size is compatible with the existing sizes of colonoscopes, but smaller sizes may be in order for smaller diameter endoscopes. The crystal must couple directly into a material with low acoustic impedance at the operating frequency. The usual materials of endoscope construction (metal, thin plastics, etc.) satisfy this requirement. The coupling into the patient's body must be accomplished by direct contact with the endoscope through the intermediate medium of a liquid or gel. The existence of an air path between the transmitter and receiver would be incompatible with ultrasonic coupling at high frequencies with small crystals. Lower frequency ultrasound can couple through air, but the resolution limit and larger crystals are incompatible with the requirements of endoscopy.

The alternate means of tracking the endoscope can be simpler but may comprise the real time display of the actual location. Possible methods include: mounting a magnet on the distal end of the endoscope and detecting and tracking its position and direction with a small movable external magnetometer applied to the abdomen; incorporating a coil and capacitor (tuned circuit) at several points along the length of the endoscope. An external movable radio frequency (RF) generator tuned to resonate with one of the internal circuits would exhibit a characteristic change in load when directed toward the endoscope resonator. A series of RF generators oscillating at different frequencies and movable over the abdomen would identify the positions of several resonators at the fundamental or harmonic frequencies; a tuned circuit in the endoscope as in the last alternative but with a set of opposing Helmholtz coils arranged to variably buck each other and create a moving nulled out zone in the region of the endoscope. Two pairs of such coils could create a null zone in X and Y coordinates covering the area of the abdomen. In operation, the null zone would be scanned over the area containing the endoscope and resonant circuit. When this zone traverses the position of the resonant circuit, the load in the system would undergo a transient due to a change in absorption of the RF energy. The X and Y coordinates of this power transient point could be displayed on a CRT.

Although particular embodiments of the invention have been described and illustrated herein, it is recognized that modifications and equivalents may readily occur to those skilled in the art and consequently it is intended that the claims be interpreted to cover such modifications and equivalents.

I claim:

1. An endoscope having an externally-controlled propulsion mechanism at the distal end, and at least one transmitter at the distal end for transmitting waves of energy to receivers adapted to be disposed on the surface of a patient for tracking the position of the distal end of said endoscope in a passage of the patient, said endoscope comprising a sheath having a window at its distal end enclosing bundles of optical fibers terminating at said window, said sheath having an inner plastic tube, an outer plastic tube, a braided metal tube between the inner and outer tubes, and a material having a shapr melting point slightly above body temperature, said material filling the interstices of the braided wire tube and the space between the plastic tubes in order that the sheath be rigid, and separate heating wires disposed in separate sections of the sheath for selective warming of said material above said melting point, thereby to make selected sections flexible.

2. An endoscope having a sheath comprised of an inner plastic tube, a braided metal tube over the inner tube, and a plastic outer tube over the braided metal tube with a material in the interstices of the braided metal tube and the space between the inner and outer plastic tubes which has a very sharp melting point slightly above body temperature, said sheath having different sections wound with insulated heating wires around the braided metal tube and inside the outer tube, and separate insulated wires inside the outer tube to the different heating wires for control of the rigidity of said sheath by sections from the proximal end of the endoscope.

* * * * *